(12) United States Patent
Prange, Jr. et al.

(10) Patent No.: US 7,462,595 B2
(45) Date of Patent: Dec. 9, 2008

(54) METHODS FOR TREATING CANCER-RELATED FATIGUE

(76) Inventors: Arthur Jergen Prange, Jr., 6503 Meadow View Rd., Hillsborough, NC (US) 27278; George Gibbs Yarbrough, 2366 NW. Pettygrove St., Portland, OR (US) 97210; Andrew Winokur, 90 Norwood Rd., West Hartford, CT (US) 06117

( * ) Notice: Subject to any disclaimer, the term of this patent is extended or adjusted under 35 U.S.C. 154(b) by 422 days.

(21) Appl. No.: 11/225,997

(22) Filed: Sep. 14, 2005

(65) Prior Publication Data

US 2006/0063703 A1  Mar. 23, 2006

Related U.S. Application Data

(60) Provisional application No. 60/629,483, filed on Nov. 19, 2004, provisional application No. 60/610,737, filed on Sep. 17, 2004.

(51) Int. Cl.
*A61K 38/00* (2006.01)
(52) U.S. Cl. ................................................ 514/2
(58) Field of Classification Search ............... 514/2
See application file for complete search history.

(56) References Cited

U.S. PATENT DOCUMENTS

| | | | | |
|---|---|---|---|---|
| 3,959,248 | A | | 5/1976 | Veber et al. ............... 530/331 |
| 4,059,692 | A | * | 11/1977 | Takahashi et al. ............ 514/18 |
| 4,299,821 | A | | 11/1981 | Kisfaludy ................... 424/177 |
| 4,563,306 | A | * | 1/1986 | Sugano et al. ............. 530/331 |
| 4,564,609 | A | | 1/1986 | Tamura ....................... 514/18 |
| 4,610,821 | A | | 9/1986 | Tamura ..................... 540/200 |
| 4,636,567 | A | | 1/1987 | Tamura ..................... 548/336 |
| 4,711,878 | A | * | 12/1987 | Sugano et al. ............... 514/18 |
| 4,719,207 | A | | 1/1988 | Tamura ..................... 514/210 |
| 4,788,179 | A | | 11/1988 | Flohe ......................... 514/19 |
| 4,877,784 | A | | 10/1989 | Kimura ................... 514/227.8 |
| 4,906,614 | A | | 3/1990 | Giertz ......................... 514/18 |
| 4,956,364 | A | | 9/1990 | Kimura ................... 514/227.5 |
| 5,151,497 | A | | 9/1992 | Uchida ...................... 530/331 |
| 5,244,884 | A | | 9/1993 | Spatola ....................... 514/18 |
| 5,405,834 | A | | 4/1995 | Bundgaard .................. 514/18 |
| 5,686,420 | A | | 11/1997 | Faden ......................... 514/18 |
| 5,811,512 | A | | 9/1998 | Hirschmann .............. 530/311 |
| 5,968,932 | A | | 10/1999 | Winokur ................. 514/227.8 |
| 6,475,989 | B1 | | 11/2002 | Sattin ......................... 514/18 |
| 6,815,425 | B1 | | 11/2004 | Meyerhoff .................. 514/18 |
| 7,067,257 | B2 | | 6/2006 | Prokai .......................... 435/6 |
| 2002/0160961 | A1 | * | 10/2002 | Ankersen .................... 514/18 |
| 2003/0166944 | A1 | | 9/2003 | Kelly | |

OTHER PUBLICATIONS

Stone (European Journal of Cancer 1998; 34: 1670-1676).*
Atkinson et al. (Oncology 2000; 14: 151-161).*
Stone et al. (European Journal of Cancer 1998; 34: 1670-1676).*

Atkinson, A. et al., NCCN Practice Guidelines for Cancer-Related Fatigue, Oncology, New York, Nov. 2000, vol. 14 (11A Suppl 10), pp. 151-161.
Bower, J. et al., Fatigue in Breast Cancer Survivors: Occurrence, Correlates, and Impact on Quality of Life, Journal of Clinical Oncology, vol. 18, No. 4, Feb. 2000, pp. 743-753.
Bower, J. et al., Fatigue and Proinflammatory Cytokine Activity in Breast Cancer Survivors, Psychosomatic Medicine, vol. 64, No. 4, 2002, pp. 604-611.
Chorvat, R.J. et al., Acetylcholine Release Enhancing Agents: Potential Therapeutics for Alzheimer's Disease, Drugs Future, vol. 20, No. 11, 1995, pp. 1145-1162.
Curt, G. et al., Impact of Cancer-Related Fatigue on the Lives of Patients: New Findings From the Fatigue Coalition, The Oncologist, vol. 5, 2000, pp. 353-360.
De Jong, N. et al., Fatigue in Patients With Breast Cancer Receiving Adjuvant Chemotherapy: A Review of the Literature, Cancer Nursing, vol. 25, No. 4, 2002, pp. 283-297.
Demetri, G. et al., Quality-of-Life Benefit in Chemotherapy Patients Treated With Epoetin Alfa Is Independent of Disease Response or Tumor Type: Results From a Prospective Community Oncology Study, Journal of Clinical Oncology, vol. 16, No. 10, Oct. 1998, pp. 3412-3425.
Dow, K. et al., An evaluation of the quality of life among long-term survivors of breast cancer, Breast Cancer Research and Treatment, vol. 39, 1996, pp. 261-273.
Gary, K. et al., The Thyrotropin-Releasing Hormone (TRH) Hypothesis of Homeostatic Regulation: Implications for TRH-Based Therapeutics, The Journal of Pharmacology and Experimental Therapeutics, vol. 305, No. 2, 2003, pp. 410-416.
Glaus, A. et al., A qualitative study to explore the concept of fatigue/tiredness in cancer patients and in healthy individuals, European Journal of Cancer Care (English language edition), vol. 5, Suppl. 2, 1996, pp. 8-23.
Greenberg, D. et al., Treatment-Related Fatigue and Serum Interleukin-1 Levels in Patients During External Beam Irradiation for Prostate Cancer, Journal of Pain and Symptom Management, vol. 8, No. May 4, 1993, pp. 196-200.
Gutstein, H., The Biologic Basis of Fatigue, 2001 Cancer, vol. 92, No. 6 Suppl., Sep. 15, 2001, pp. 1678-1693.
Holley, S., Cancer-Related Fatigue: Suffering a Different Fatigue, 2000, Cancer Practice, Mar./Apr. 2000, vol. 8, No. 2, pp. 87-94.
Irvine, D. et al., The prevalence and correlates of fatigue in patients receiving treatment with chemotherapy and radiotherapy, Cancer Nursing, vol. 17, 1994, pp. 367-378.
Kunkel, E., et al., Biopsychosocial Aspects of Prostate Cancer, Psychosomatics, vol. 41, No. 2, Mar.-Apr. 2000, pp. 85-94.
Kurzrock, R., The Role of Cytokines in Cancer-Related Fatigue, 2001 Cancer, vol. 92, No. 6 Suppl., Sep. 15, 2001, pp. 1684-1688.
Mendoza, T. et al., The Rapid Assessment of Fatigue Severity in Cancer Patients: Use of the Brief Fatigue Inventory, Cancer, 1999, vol. 85, No. 5, Mar. 1, 1999, pp. 1186-1196.

(Continued)

*Primary Examiner*—Brandon J Fetterolf
(74) *Attorney, Agent, or Firm*—Martin Savitzky

(57) ABSTRACT

Methods for treating cancer patients suffering from severe and persistent fatigue, diagnosed as Cancer-Related Fatigue (CRF), with thyrotropin-releasing hormone (TRH) and peptidomimetic analogs of TRH.

10 Claims, No Drawings

OTHER PUBLICATIONS

Mock, V., Fatigue Management: Evidence and Guidelines for Practice, Cancer 2001, vol. 92, No. 6 Suppl., Sep. 15, 2001, pp. 1699-1707.

Portenoy, R. et al., Cancer-Related Fatigue: Guidelines for Evaluation and Management, The Ongologist, vol. 4, 1999, pp. 1-10.

Richardson, A., Fatigue in cancer patients: a review of the literature, European Journal of Cancer Care (English language edition), vol. 4, 1995, pp. 20-32.

Smets, E. et al., The Multidimensional Fatigue Inventory (MFI) Psychometric Qualities of an Instrument to Assess Fatigue, Journal of Psychosomatic Research, vol. 39, No. 5, 1995, pp. 315-325.

Smets, E. et al., Application of the multidimensional fatigue inventory (MFI-20) in cancer patients receiving radiotherapy, British Journal of Cancer, vol. 73, No. 2, 1996, pp. 241-245.

Stone, P. et al., A study to investigate the prevalence, severity and correlates of fatigue among patients with cancer in comparison with a control group of volunteers without cancer, Ann Oncology, vol. 11, 2000, pp. 561-567.

Stone, P. et al., Fatigue in Patients with Cancer, European Journal of Cancer, vol. 34, No. 11, 1998, pp. 1670-1676.

Valentine, A. et al., Cognitive and Mood Disturbance as Causes and Symptoms of Fatigue in Cancer Patients, Cancer 2001, vol. 92, No. 6 Suppl., Sep. 15, 2001, pp. 1694-1698.

Visser, M. et al., Fatigue, depression and quality of life in cancer patients: how are they related?, Support Care Cancer, vol. 6, 1998, pp. 101-108.

Ware, J. et al., The MOS 36-Item Short-Form Health Survey (SF-36): Conceptual Framework and Item Selection, Medical Care, vol. 30, No. 6, Jun. 1992, pp. 473-483.

WHO Drug Information, vol. 1, No. 3, 1987, pp. 184.

WHO Drug Information, vol. 2, No. 3, 1988, pp. 166.

Yamamura, M. et al., Synthesis and Pharmacological Action of TRH analog peptide (Taltirelin), Nippon Yakurigaku Zasshi, vol. 110, Suppl. 1, 1997, pp. 33P-38P.

Yarbrough, G. et. al., Thyrotropin-releasing hormone (TRH) in the neuroaxis: Therapeutic effects reflect physiological functions and molecular actions, Medical Hypotheses, 2007, pp. 1-8.

Zigmond, A. et al., The Hospital Anxiety and Depression Scale, Acta Psychiatr. Scand., vol. 67, 1983, pp. 361-370.

* cited by examiner

METHODS FOR TREATING CANCER-RELATED FATIGUE

CROSS REFERENCE

This application claims priority to and incorporates by reference U.S. Provisional Application Nos. 60/610,737, filed Sep. 17, 2004, and 60/629,483, filed Nov. 19, 2004.

FIELD OF THE INVENTION

The present invention relates to the treatment of metabolic, immunological and central nervous system disturbances presenting as severe and persistent fatigue in patients suffering from and treated for neoplastic diseases.

Cancer-related fatigue (CRF) is the most widespread adverse symptom related to cancer and cancer therapy. In a recent study, cancer patients reported that fatigue is the most distressing symptom associated with their cancer and cancer treatment (Richardson et al, 1995). CRF is a multicausal, multidimensional, and complex disturbance and hence is difficult to describe for patients, their families and even for health care providers (Portenoy et al, 1999). Despite these complexities and difficulties, considerable progress has been made in differentiating CRF from other forms of fatigue that healthy individuals may experience (Stone et al, 2000). CRF can be best defined as an unusual and persistent sense of tiredness that can occur with cancer and cancer therapy (Atkinson et al, 2000). CRF may affect both physical and mental capacity and is unrelieved by rest. It is more severe, more energy draining, longer lasting and more unrelenting than other forms of fatigue (Glaus et al, 1996). CRF interferes with usual functioning and has a devastating effect on almost all aspects of patients' lives. It has a pervasive effect on motivation. Additionally, attending and completing a task becomes difficult. The most unusual characteristic of CRF is that it is unrelieved by rest or additional sleep (Holly, 2000). For most cancer patients, CRF is very different from anything they have previously experienced. Most of the current pharmacological and non-pharmacological treatments offered by health care professionals are based on anecdotal evidence.

As novel and more effective cancer treatments have led to longer survival, CRF and quality of life issues related to CRF have taken center stage as fatigue has become more intense and distressing (Curt et al, 2000). Better and more sensitive screening instruments such as the brief fatigue inventory (BFI) have been developed to identify CRF (Mendoza et al, 1999). Also, comprehensive instruments such as the multidimensional fatigue inventory (MFI) are now available to assess the complex symptomatology of CRF (Smets et al, 1995 and Smets et al, 1996).

Studies examining the prevalence of fatigue among breast cancer patients have found that up to 99% experience some level of fatigue during the course of radiation therapy and/or chemotherapy, and more than 60% rate their level of fatigue as moderate to severe (Stone et al, 1994). Studies have also shown that the intensity and duration of fatigue experienced by breast cancer patients undergoing treatment is significantly greater than that experienced by healthy controls (Irvine et al, 1994). There is growing evidence to suggest that fatigue may persist for months or even years after completion of breast cancer treatment, particularly among patients who have received adjuvant chemotherapy (de Jong et al, 2002). Evidence also suggests that years after diagnosis and treatment, fatigue continues to exert a negative impact on overall quality of life among breast cancer survivors and causes greater interference with daily functioning in survivors than in healthy controls (Dow et al, 1996). Patients with prostate cancer have reported similar high rates of fatigue with or without treatment (Kunkel et al, 2000).

Five factors are highly correlated with CRF: anemia, hypothyroidism, pain, sleep disturbance, and emotional distress (Mock et al, 2001). Emotional distress ranges from stress, minor depression, and restlessness to symptoms meeting criteria for major depressive disorder or an identifiable anxiety disorder (Valentine & Myers, 2001). Studies have shown that pain, sleep disturbance, and depression are positively correlated to CRF. However, this relationship does not imply causality. A number of studies failed to find a significant cause-effect relationship between these factors and the development of CRF. Visser and Smets (1998) failed to find such a relationship between depression and fatigue in patients treated with radiation therapy, although both symptoms predicted decreased quality of life. In a study conducted by Bower et al (2000), pain, depression and sleep disturbance strongly predicted fatigue in breast cancer survivors, but the study failed to find a cause-effect relationship for any of the three variables.

These findings underscore the fact that CRF is probably an independent entity and may remain refractory to treatment after adequate treatment of other symptoms. The outcomes of the studies cited above suggest that several of these factors are interrelated in a network of symptoms with fatigue and may have common or overlapping physiologic/biochemical mechanisms (de Jong et al, 2002). Basic mechanisms of CRF can be arbitrarily divided into two major components: peripheral mechanisms leading to energy imbalance, and central mechanisms, which encompass changes in function of the hypothalamic-pituitary-adrenocortical (HPA and)/hypothalamic-pituitary-thyroid (HPT) axes as well as intrinsic changes in neural circuitry underlying fatigue and arousal (Gutstein, 2001). The processes leading to negative energy balance are quite diverse.

Recent studies imply a role for HPA axis dysregulation (especially cortisol) and for certain endogenous pro-inflammatory cytokines (IL-1, IL-6, IFN, TNF) aberrantly produced in many cancers/cancer treatments (Kurzock, 2001). Greenberg et al. (1993) reported significant increase in fatigue level and interleukin-1 (IL-1) beta levels among prostate cancer patients in the acute phase of radiation therapy. Bower et al. (2002) examined selected sensitive markers of inflammatory activity in breast cancer survivors. These markers included interleukin-1 receptor antagonist (IL-1ra), soluble tumor necrosis factor-receptor type II (TNF-RII) and neopterin. IL-1ra level highly correlates with IL-1 level; TNF-RII levels correlate with TNF-alpha levels and reflect TNF-alpha activity. Neopterin is secreted by activated macrophages, the primary source of proinflammatory activity. Fatigued breast cancer survivors had significantly higher levels of these markers of proinflammatory activity and lower serum levels of cortisol than the non-fatigued group.

The HPT Axis and TRH

In 1969 groups led by R Guillemin and A Schally independently announced that the hypothalamic substance that causes the anterior pituitary gland to release thyroid-stimulating hormone is L-pyroglutamyl-L-histidyl-L-prolineamide (pGlu-His-ProNH$_2$). On the basis of this biological activity, the tripeptide is known as thyrotropin-releasing hormone (TRH).

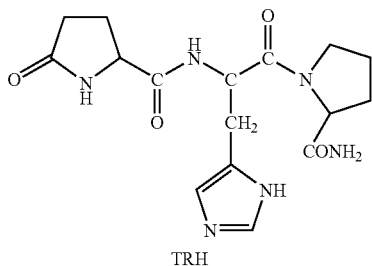

TRH

There are nearly 14,000 publications on TRH in the PubMed database alone, reporting a widely diverse set of physiologic findings. The breadth and scope of these reports are both remarkable and confusing. Administration of TRH to laboratory animals results in a totally unexpected spectrum of extrahypothalamic biological effects. Perhaps the most unique effects of TRH reside in its 'analeptic' actions to offset the sedation and behavioral depressant effects of virtually all classes of drugs, including alcohol, general anesthetics and other psychoactive drugs. TRH will even arouse hibernating animals. Conversely, TRH has actions in the opposite direction from these arousing, alerting effects including anticonvulsant and anti-anxiety activities. And interestingly, TRH has little demonstrable activity in normal experimental animals. TRH was found to have definite, albeit brief, antidepressant effects in patients with major unipolar depression. These findings, confirmed by many but not all investigators, more than any other, provided the basis for the subsequent interest in both the basic and clinical neuropharmacology of TRH.

One proposed unifying hypothesis for these diverse findings suggested that TRH functions as an endogenous 'ergotropic' substance to raise and maintain CNS arousal and vigilance. Although TRH does have alerting, arousing, and analeptic properties, this hypothesis failed to account for the apparent state-dependent effects of TRH. Thus, TRH has few effects in normal subjects and in some circumstances TRH can cause tropotrophic effects to reduce CNS excitability. To account for all the properties of TRH, it was proposed recently that the main function of TRH is to promote homeostasis by state-dependent normalization of CNS activity and autonomic nervous system activity. The foregoing points along with related observations are detailed in Gary et. al., *The thyrotropin-releasing hormone (TRH) hypothesis of homeostatic regulation: implications for TRH-based therapeutics. J Pharmacol Exp Ther.* 2003 May; 305(2): 410-6. (Epub 2003 Feb. 20). This hypothesis is consistent with the traditional role of TRH as a regulator of metabolic homeostasis through its effects on the thyroid system.

TRH itself is a poor drug candidate because, like all peptides, it is poorly absorbed, rapidly degraded by peptidases and has a half-life in plasma of approximately five minutes. Its short half-life makes it difficult to interpret negative results. Consequently, TRH administered peripherally has limited ability to reach the central nervous system to produce its behavioral effects. Nonetheless, there are many reports of TRH as well as metabolically stable TRH analogs, and prodrugs thereof, that are described as useful in numerous CNS disorders.

Reported Developments

Occasionally, the clinician may identify a reversible cause of fatigue for which there is a readily available treatment (e.g. erythropoietin for fatigue related to anemia). Anemia, hypothyroidism, electrolyte abnormalities (hypomagnesemia, hypokalemia) are some of the medically reversible causes of CRF (Mock, 2001). These major medically reversible causes of CRF may be identified in almost 50% of patients experiencing CRF (Demetri et al, 1998). However, the fact remains that in the remaining 50% of patients the etiology remains unknown despite a comprehensive work-up. The etiology and/or pathophysiology in such cases, hereinafter referred to as "idiopathic CRF", are probably related to more complex, unidentified centrally driven mechanisms.

Today, only one drug on the market, modafinil (Provigil), would appear to be useful for the treatment of idiopathic CRF. However, modafinil is a psycho-stimulant and therefore is classified as a Schedule IV drug by the FDA in recognition of its addiction potential.

TRH (and some TRH analogs) has been tested in depression, amyotrophic lateral sclerosis, Alzheimer's disease, vascular dementia, 'disturbances of consciousness', neonatal respiratory distress, certain rare epilepsies, stroke, spinal muscular atrophy, and spinocerebellar degenerative disease. Each of these efforts has been based on a different aspect of the broad pharmacology of TRH. In most instances both positive and negative results have been observed. To our knowledge there are no neurological or psychiatric disorders where the etiology or symptoms are known to be a direct result of a specific deficit in TRH. Consequently, such diverse and equivocal findings often have led to a negative view of the usefulness of TRH-based drugs. Nonetheless, TRH and many TRH analogs have been proposed for use in a variety of neurological disorders.

TRH analogs, such as taltirelin, are disclosed in U.S. Pat. Nos. 4,711,878 and 4,563,306, both assigned to Tanabe Seiyaku Pharmaceutical Co., Ltd. (useful in treating consciousness disorders, short attention span, speech disorders, hypobulia, Lennox syndrome, senile dementia, hypnotic intoxication, autism, hyperkinesia, schizophrenia, depression and Parkinsonism).

Other TRH analogs, such as MK-771, are disclosed in U.S. Pat. No. 3,959,248, assigned to Merck & Co, Inc. (useful for treating central nervous system depression and/or patients in need of thyrotropin release activation).

Histidyl peptide derivatives of TRH, such as JTP-2942, are disclosed in U.S. Pat. No. 5,151,497, assigned to Japan Tobacco Inc and Yoshitomi Pharmaceuticals, Inc (useful in treating central nervous disorders such as impaired consciousness, depression, hypomnesia, the like in association with schizophrenia, melancholia, senile dementia, sequelae of cerebrovascular disorders, head trauma, epilepsy, and spinocerebellar degeneracy).

CNS active substituted azetidinone TRH analog compound, such as YM-14637 (azetirelin), are disclosed in U.S. Pat. Nos. 4,636,567; 4,610,821; 4,564,609, and 4,719,207, all of which are assigned to Yamanouchi Pharmaceutical Co., Ltd. (useful for improving disturbance of consciousness in schizophrenia, nervous depression, the sequels to cerebrovascular disorders, head injury, senile dementia, epilepsy, etc., or improving hypobulia, depressive syndrome, and memory loss).

TRH analogs related to RGH-2022 (positirelin), useful in treating central nervous system disorders, are disclosed in U.S. Pat. No. 4,368,073 assigned to Patentbureau DANUBIA, and U.S. Pat. No. 4,299,821, assigned to Richter Gedeon.

Iodinated analogs of TRH are disclosed in U.S. Pat. No. 5,244,884, assigned to USA Dept of Health (useful in treating depression, circulatory shock, ALS, spinal cord injury and hypertension).

Histidylprolineamide TRH derivatives related to CG-3703 (montirelin): are disclosed in U.S. Pat. No. 4,877,784, assigned to Nippon Shinyaku Pharmaceutical Co., Ltd, (useful in treating of epilepsy). Histidyl substituted TRH analogs are disclosed in U.S. Pat. No. 6,475,989 (useful for the treatment of neurological and neurobehavioral disorders) and U.S. Pat. No. 5,686,420, assigned to Georgetown University (used to treat brain and spinal cord injuries caused by central nervous system trauma, and patients undergoing a tissue transplant by reducing secondary traumatic injury associated with the transplant process).

TRH peptidomimetics and related cyclic hexapeptides are disclosed in U.S. Pat. No. 5,811,512, assigned to the University of Pennsylvania (use as substance P antagonists for the control and/or treatment of anxiety, psychosis and schizophrenia; neurodegenerative disorders such as senile dementia of the Alzheimer type, Alzheimer's disease and Down's syndrome; respiratory diseases such as bronchospasm and asthma; inflammatory diseases such as inflammatory bowel disease, osteoarthritis and rheumatoid arthritis; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception). TRH analogs, useful for treating neurological disorders, wherein the N-terminal moiety comprises one of five different ring structures and the histidyl moiety is substituted with CF3, NO2 or a halogen, are disclosed in U.S. Pat. No. 5,686,420 assigned to Al Faden. A method of treating and preventing diseases and injuries of the brain, spinal cord and retina by administering to a subject the peptide pGLU-GLU-PRO-NH2 alone or in combination with a nitrone is disclosed in U.S. Pat. No. 6,815,425 assigned to J L Meyerhoff et. al. Prodrugs of TRH characterized by having a higher lipophilicity than TRH and possessing a high resistance toward degradation by TRH-inactivating enzymes are disclosed in U.S. Pat. No. 5,405,834 assigned to H Bundgaard and J Moss.

Peptide derivative compounds related to inhibitors of TRH degrading enzyme (TRH-DE) are disclosed in U.S. Patent Application Publ. No. 20030166944. U.S. Patent Application Publ. No. 20030232966 (L Prokai at Univ Florida) discloses that pyridinium analogs of TRH are useful in treating diverse physical and neurological conditions such as fatigue, depression, schizophrenia, circulatory shock, amyotrophic lateral sclerosis, and hypertension, mental disorders including depression, dementia, and schizophrenia; encephalomyelitis including so-called chronic fatigue syndrome; brain diseases including leukodystrophy, adrenoleukodystrophy, migraines, epilepsy, Alzheimer's disease, Parkinsonian disorders, cerebral palsy, and Huntington disease; brain or spinal cord trauma (i.e., stroke, brain hypoxia); and motorneuron diseases/disorders including Tourette Syndrome).

Prior art disclosing additional conditions where TRH analogs have been disclosed as useful include the following: U.S. Pat. No. 5,968,932, assigned to Gruenthal GmbH for inhibiting sleep apnea; U.S. Pat. No. 4,956,364, assigned to Nippon Shinyaku Co., Ltd, as nootropic agents for treating senile dementia; U.S. Pat. No. 4,906,614, assigned to Gruenthal GmbH; for treating posttraumatic nervous injuries; and U.S. Pat. No. 4,788,179, assigned to Gruenthal GmbH for treating amyotrophic lateral sclerosis.

The peptidomimetic, taltirelin, has been extensively studied and demonstrated to be a metabolically stable TRH analog with robust CNS effects. Yamamura et al. (1997) reviewed the actions of taltirelin in basic science studies showing that the effects of taltirelin that run parallel to actions of TRH. Taltirelin has already been shown to have some efficacy in the treatment of spinocerebellar degeneration (SCD), slowing the progression of this severe neurological disorder, and it has been approved since 2000 and is marketed for the treatment of SCD in Japan. In both Phase III clinical trials and in post-marketing surveillance in Japan, since its launch in 2001, taltirelin has been demonstrated to have an excellent safety record and a very favorable side effect profile. It is reported to relieve the ataxias of these patients, to decrease their needed visits to the hospital and to improve their overall quality of life. The drug is also finding utility in other 'off-label' neurological indications such as some childhood epilepsies and in managing patients with spinal muscular atrophies. As with other such metabolically stable TRH analogs developed to date the CNS effects of taltirelin far exceed its transient TSH-releasing endocrine effects.

Another TRH analog is montirelin available from Grünenthal, BRD. Montirelin is a long-acting TRH analog, having antidepressive and CNS stimulating effects. and is reported to be useful as a potential nootropic and psychostimulant. WHO Drug Information 1(3): 184, 1987; WHO Drug Information 2(3): 166, 1988; Chorvat R J, Earl R A, Zacvek R: Acetylcholine release enhancing agents: potential therapeutics for Alzheimer's disease. Drugs Future 20/11: 1145-1162, 1995.13 *Montirelin's chemical name is* (6-methyl-5-oxo-3-thiomorpholinyl)carbonyl-histidylprolinamide or N-[[(3R, 6R)-6-methyl-5-oxo-3-thio-morpholinyl]carbonyl]-L-histidyl-L-prolinamide.

In Gary et. al., *The thyrotropin-releasing hormone (TRH) hypothesis of homeostatic regulation: implications for TRH-based therapeutics. J Pharmacol Exp Ther.* 2003 May; 305 (2): 410-6. Epub 2003 Feb. 20, the authors reported that main neurobiological function of TRH is to promote homeostasis, and suggest that TRH and TRH analogs may be useful in a variety of therapeutic indications including, among others, depression, chronic fatigue syndrome, narcolepsy, and sedation secondary to drugs, chemotherapy or radiation therapy, None of the foregoing prior art references suggests that TRH or any TRH analog would be useful to treat the persistent and severe fatigue uniquely experienced by cancer patients and diagnosed as idiopathic CRF. Patients suffering from cancer-related fatigue, and in particular, idiopathic cancer-related fatigue, which is persistent and severe in nature, are presently without effective treatments. The present invention is intended to offer these patients relief.

SUMMARY OF THE INVENTION

The present invention relates to a method for the treatment of cancer-related fatigue in human patients suffering from a neoplastic disorder, comprising administering a therapeutically effective cancer-related fatigue relieving amount of TRH or a TRH analog, its pharmaceutically acceptable salts, or prodrug thereof. More particularly, a preferred aspect of the present invention comprises treating idiopathic cancer-related fatigue in a patient exhibiting severe and persistent fatigue comprising administering to said patient fatigue-relieving effective amount of TRH or a metabolically stable TRH analog, its pharmaceutically acceptable salts, or prodrug thereof. A most preferred embodiment of the TRH analog for use in the present is the TRH analog, taltirelin, its hydrates, prodrugs, and its pharmaceutically acceptable salts.

DETAILED DESCRIPTION

The term "cancer-related fatigue-relieving amount" means that amount of a drug or pharmaceutical agent that will elicit the biological or medical response of a human that is being sought by a medical doctor or other clinician. In particular, with regard to treating cancer-related fatigue, the "relieving amount" is intended to mean that effective amount of TRH or the TRH analog or prodrug of TRH or the TRH analog that will bring about the fatigue-relieving response that is being sought.

The term "pharmaceutically acceptable salt," describes any pharmaceutically acceptable form (i.e., ester, mono-, di-, or tri-phosphate ester, salt of an ester or a related group) of TRH or TRH analogs, which, upon administration to a patient, provides TRH or a TRH analog. Pharmaceutically acceptable salts include those derived from pharmaceutically acceptable inorganic or organic bases and acids. Suitable salts include organic moieties such as acetate, trifluoroacetate, oxalate, valerate, oleate, laurate, benzoate, lactate, tosylate, citrate, maleate, fumarate, succinate, tartrate naphthalate, and those derived from such inorganic moieties as Group I (i.e., alkali metal salts, potassium and sodium), Group II (alkaline Earth metal salts, calcium and magnesium), ammonium and protamine, zinc, iron with counter ions such as chloride, bromide, sulfate, phosphate, among numerous other acids well known in the pharmaceutical art.

The term "prodrug" denotes a molecule that is incapable of exerting the pharmacological activity of the active compound. The active compound will exert its therapeutic effects after it is bioactivated from the transient modified form (i.e., oxidation of a dihydropyridine to a pyridinium or hydrolysis of an ester moiety to provide a carboxylic acid). Non-limiting examples of methods for bioactivating a prodrug include oxidation, reduction, amination, deamination, hydroxylation, dehydroxylation, alkylation, dealkylation, acylation, deacylation, phosphorylation, and dephosphorylation. Prodrugs of TRH or TRH analogs may be converted in vivo into biologically active, therapeutic compounds by endogenous enzymes. Prodrug forms of TRH or TRH analogs may overcome problems associated with stability, water-solubility, toxicity, lack of specificity, or limited bioavailability, that exists with TRH and its traditional analogs. Prodrugs of TRH or TRH analogs may exhibit improved blood brain barrier penetration when compared to TRH and traditional TRH analogs.

The term "treating" refers to alleviating the disorder or condition to which the term "treating" applies, including one or more symptoms of such disorder or condition. The related term "treatment," as used herein, refers to the act of treating a disorder, symptom, or condition, as the term "treating" is defined above.

Therapeutic methods according to the present invention include the controlled administration to a patient of an effective amount of TRH or at least one or more of the TRH analogs to provide therapy. The administration of TRH or TRH analogs to a patient may comprise from one to several oral administrations per day (for example, B.I.D or Q.I.D.), parenteral administration, including intravenous (bolus or continuous intravenous drip) and intramuscular, topical, subcutaneous, transdermal (which may include a penetration agent), buccal and suppository administration, among other routes of administration. The therapeutic dose of TRH or the TRH analog, its pharmaceutically acceptable salt or prodrug thereof, depends on the route of administration; the age, weight and condition of patients; and the particular disease to be treated. In general, however, it may be used at a dose of 0.0005 to 5 mg/kg/day, especially at a dose of 0.01 to 2 mg/kg/day in the case of oral administration; or at a dose of 0.001 to 0.1 mg/kg/day in the case of parenteral administration (e.g. intravenously, intramuscularly, subcutaneously).

Patients experiencing CRF may be treated with an effective fatigue-relieving amount TRH or of a TRH analog in the amount of about 5 mg to about 30 mg from once to three times a day, preferably, from about 5 mg/day to about 20 mg/day, and most preferably from about 5 mg/day to about 15 mg/day, for a period of time of about one to about four weeks, or until the patient reports significant reduction in fatigue level. A preferred embodiment of the present invention comprises the administration of about 5 to about 10 mg/day for about one to about four weeks. Patients who have their fatigue rating reduced significantly during the treatment are placed on a one to two week decreasing dosage schedule.

The patient population benefiting most from the present invention includes those cancer patients who exhibit persistent and severe idiopathic fatigue more than about a week subsequent to their treatment with chemotherapy, radiation, immunotherapeutics, and/or surgery. We believe that such patients may be identified in accordance with the evaluation criteria described below, as well as by critical immune and HPA axis 'markers' characteristic of the pathophysiology underlying idiopathic CRF. The following study description is exemplary of such patient population selection and a preferred embodiment of a protocol for treating idiopathic cancer-related fatigue.

EXAMPLE

Selection and Treatment Study—TRH

Patient Selection. Patients with a diagnosis of cancer, in this study, breast cancer; or prostate cancer, are screened for CRF using a brief fatigue inventory (BFI) in an oncology clinic setting. The BFI is a simple 9-item self-administered scale and requires about 5-10 minutes to complete. Patients experiencing a severe level of fatigue (BFI$\geq$7) are identified based on this screening. These patients then undergo additional screening with a comprehensive interview and laboratory assessments (hemoglobin, hematocrit, thyroid stimulating hormone concentration, and electrolytes) to identify and exclude patients with medically reversible or other treatable causes of fatigue (viz. anemia, hypothyroidism, electrolyte abnormalities, significant pain dominating the CRF presentation). A total of 20 patients with severe CRF and without any medically reversible or other treatable causes of CRF are identified based on the initial screening process. Medically reversible or other treatable causes of CRF may be present in as many as 50% of patients with cancer and/or undergoing cancer therapy. (Demetri et al, 1998). Hence approximately 40 patients with the breast or prostate cancer diagnoses are screened to identify the 20 patients with idiopathic CRF.

The patients selected undergo a comprehensive assessment to investigate different aspects of fatigue. This assessment consists of the multidimensional fatigue inventory (MFI), a 20-item scale (Smets et al, 1995 and Smets et al, 1996) and a quality of life questionnaire, the 36-item short form survey (SF-36) (Ware and Sherbourne, 1992). Patients are evaluated for two major psychiatric disorders frequently co-occurring with CRF, depressive disorders and anxiety disorders. This is accomplished using the hospital anxiety and depression scale (HADS). The HADS is a 14-item screening tool. It consists of separate scales for anxiety (HADA) and depression (HADD). Its effectiveness is relatively unaffected by the presence of concurrent physical illness (Zigmond and Snaith, 1983).

Additionally, patients undergo specific laboratory assessments related to immune and HPA axis function.

In the intervention phase of the study, patients receive infusions of TRH (0.5 mg or 1.5 mg) or saline as placebo at weekly intervals for 4 weeks. Assignment of TRH or saline will be double-blind and randomized following an ABBA design. For TRH infusions, each subject receives the 0.5 mg dose on the first active drug infusion trial, and the 1.5 mg dose of TRH on the second active infusion trial. Patients undergo fatigue assessments with the BFI and MFI each week on the day of infusion at the GCRC and for the following two days, they complete rating scales from home. They also undergo quality of life assessments with the SF-36 and depression and anxiety assessment with the HADS at randomization and at the end of the intervention phase. Patients are assessed for their overall status using the clinical global impression of severity of illness scale (CGI-S) at randomization and at each week during the 4-week intervention phase. At baseline and at each week throughout the intervention phase, patients again undergo laboratory assessments for the immune factors and HPA axis markers described below.

Patient Selection—Inclusion/Exclusion Criteria

Inclusion Criteria for Entering the Initial Screening Phase:
1. Provide written consent before initiation of any study-related procedures.
2. Male or Female, 18 years of age or older with a diagnosis of breast cancer or prostate cancer.
3. Able to understand and comply with the requirements of the study.

Exclusion Criteria to Enroll in the Initial Screening Phase:
1. Patients with an identifiable diagnosis of substance abuse or dependence within 6 months prior to evaluation (except in full remission, and except for caffeine or nicotine dependence) as defined by DSM-IV criteria.
2. Patients with any significant unstable or inadequately treated co-morbid medical condition that would confound evaluation of CRF (e.g. diabetes, CHF, history of other cancers) as judged by the investigator.
3. Patients with any significant unstable or inadequately treated psychiatric disorder (except depressive and/or anxiety disorders) confounding appropriate CRF assessment as judged by the investigator.
4. Patients on multiple psychotropic medications.
5. Patients with a history of immunologically related diseases or diseases that could affect immune system function.
6. Patients regularly using immunosuppressive medications.
7. Patients with diseases that clearly affect the hypothalamic-pituitary-adrenocortical (HPA) axis function or patients on hormonal treatments affecting the HPA axis.
8. Any other condition, which, in the opinion of investigator, would make the patient, unsuited for enrollment or could interfere with the patient's participation in the study.

Additional Exclusion Criteria for Entering the Second, Comprehensive Assessment Phase:

Any of the following is regarded as a criterion for exclusion from the entering the second, comprehensive fatigue assessment phase of the study (based on the initial screening and laboratory assessment):
1. Patients with medically reversible causes of CRF such as anemia, hypothyroidism, and electrolyte abnormalities.
2. Patients with potentially treatable associated symptoms dominating the CRF scenario such as pain, which may have a causal relationship to CRF.

Criteria for Discontinuation:

Patients may be discontinued from the study treatment and assessments at any time. Specific reasons for discontinuing a patient from the study are as follows:
1. Voluntary discontinuation by the patient who is at any time free to discontinue participation in the study.
2. Severe non-compliance to the protocol as judged by the investigator.
3. Incorrect enrollment.
4. Patient is hospitalized due to any condition during the study period.

Study Design:

The study utilizes a double-blind, placebo-controlled crossover design. Over a four week period at weekly intervals, patients are evaluated in the General Clinical Research Unit (GCRC) of the John Dempsey Hospital and receive intravenous infusions of TRH (0.5 mg for the first active drug trial, 1.5 mg for the second active drug trial) or saline in random order following an ABBA crossover design.

Initial screening phase. Patients with a breast cancer or prostate cancer diagnosis meeting the initial inclusion and exclusion criteria undergo an initial screening with the brief fatigue inventory (BFI) in an oncology clinic setting. Patients experiencing a severe level of fatigue (BFI$\geq$7) are identified based on this screening. These patients will undergo additional screening with a comprehensive interview and laboratory assessments (hemoglobin, hematocrit, thyroid stimulating hormone level and electrolytes) to identify and exclude patients with medically reversible or other treatable causes of fatigue (viz., anemia, hypothyroidism, electrolyte abnormalities, significant pain dominating the CRF scenario). A total of 20 patients with severe CRF and without any medically reversible causes of CRF are identified based on the initial screening process.

Selected patients undergo a comprehensive assessment to investigate different aspects of fatigue and quality of life. This assessment consists of the multidimensional fatigue inventory (MFI) and the quality of life questionnaire, the 36-item short form survey (SF-36). Patients are also evaluated for depressive disorders and anxiety disorders using the hospital anxiety and depression scale (HADS). Patients are assessed for their overall status using the clinical global impressions severity of illness scale (CGI-S) and clinical global impressions improvement scale (CGI-I) at randomization and each week during the 4-week intervention phase. Additionally, patients undergo specific laboratory assessments related to immune and HPA axis. These laboratory assessments include selected serum markers for inflammatory activity and marker for HPA axis. The immune makers include interleukin-1 receptor antagonist (IL-1ra), soluble tumor necrosis factor receptor type II (sTNF-RII) and neopterin. Serum cortisol levels serve as a marker for the HPA axis. Heightened levels of one or more of these markers appear to be related to the pathophysiological mechanisms underlying CRF, and their reduction reflects the effect of treatment intervention.

Assessments. Patients undergo fatigue assessments with the BFI and MFI at baseline and at each week during the 4-week study course. Patients also undergo assessments with SF-36, HADS and CGI-S at randomization and at each week during the 4-week intervention phase. The CGI-I is performed at weekly intervals during the 4-week intervention phase. At baseline and at each week during the 4-week treatment intervention phase, patients undergo laboratory assessments for immune factors and HPA axis markers noted above.

Analysis:

Administration of thyrotropin releasing hormone at either 0.5 mg or 1.5 mg is superior to placebo in improving cancer related fatigue as measured by change from baseline in mean fatigue scores assessed using the BFI and MFI at each of the comparisons points during the 4 week treatment intervention phase.

Thyrotropin releasing hormone (0.5 mg or 1.5 mg) is superior to placebo in improving quality of life as measured by change from baseline in mean quality of life scores assessed using SF-36 after 6 weeks of treatment Other variables evaluated to assess efficacy include (1) the change from baseline in the mean of the CGI and CGI-S scores, and (2) markers of immune and HPA axis function as measured by assessment of IL-1ra, TNF-RII, neopterin and cortisol level to assess effects of TRH on the immune and HPA axis function.

Variables for Safety Analysis:

Safety and tolerability will be assessed by statistical analysis and clinical review of the following data collected during the study: Adverse experiences (Ae's), reason for discontinuation due to AE's, laboratory values, ECG, physical examination and vital signs.

Approaches to Analysis:

The primary study population used for efficacy analyses is the full analysis set (FAS). The FAS includes all patients who take study medication and have had at least one post randomization assessment. The last observation carried forward (LOCF) analysis is conducted to address any dropout issues. Primary efficacy analyses are performed using analysis of covariance.

EXAMPLE

Selection and Treatment Study—TRH Analog

Patient Selection. Patients with a diagnosis of cancer, in this study, breast cancer, or prostate cancer, are screened for CRF using a brief fatigue inventory (BFI) in an oncology clinic setting. The BFI is a simple 9-item self-administered scale and requires about 5-10 minutes to complete. Patients experiencing a severe level of fatigue (BFI$\geq$7) are identified based on this screening. These patients then undergo additional screening with a comprehensive interview and laboratory assessments (hemoglobin, hematocrit, thyroid stimulating hormone concentration, and electrolytes) to identify and exclude patients with medically reversible or other treatable causes of fatigue (viz. anemia, hypothyroidism, electrolyte abnormalities, significant pain dominating the CRF presentation). A total of 40 patients with severe CRF and without any medically reversible or other treatable causes of CRF are identified based on the initial screening process. Medically reversible or other treatable causes of CRF may be present in as many as 50% of patients with cancer and/or undergoing cancer therapy. (Demetri et al, 1998). Hence approximately 60-70 patients with the breast or prostate cancer diagnoses are screened to identify the 40 patients with idiopathic CRF. Identified patients are randomized into two groups of 20 patients each, which are a study medication group and a placebo group.

Both groups undergo a comprehensive assessment to investigate different aspects of fatigue. This assessment consists of the multidimensional fatigue inventory (MFI), a 20-item scale (Smets et al, 1995 and Smets et al, 1996) and a quality of life questionnaire, the 36-item short form survey (SF-36) (Ware and Sherbourne, 1992). Patients are also evaluated for two major psychiatric disorders frequently co-occurring with CRF, depressive disorders and anxiety disorders. This is accomplished using the hospital anxiety and depression scale (HADS). The HADS is a 14-item screening tool. It consists of separate scales for anxiety (HADA) and depression (HADD). Its effectiveness is relatively unaffected by the presence of concurrent physical illness (Zigmond and Snaith, 1983). Additionally, patients from both the groups undergo specific laboratory assessments related to immune and HPA axis function.

In the intervention phase of the study, patients receive study medication or placebo based on their group assignments. Patients undergo fatigue assessments with BFI and MFI every week during the intervention phase. They also undergo quality of life assessments with the SF-36 and depression and anxiety assessment with the HADS at randomization, at week 4 and at the end of the intervention phase. Patients are assessed for their overall status using the clinical global impressions severity of illness scale (CGI-S) at randomization, at week 4 and at the end of the intervention phase. They are also assessed for any global improvement using clinical global impressions improvement scale (CGI-I) at week 4 and at the end of intervention phase. At the end of the intervention phase, patients again undergo laboratory assessments for the same immune and HPA axis markers conducted after the initial screening.

Patient Selection—Inclusion/Exclusion Criteria

Inclusion Criteria for Entering the Initial Screening Phase:
1. Provide written consent before initiation of any study-related procedures.
2. Male or Female, 18 years of age or older with a diagnosis of breast cancer or prostate cancer.
3. Able to understand and comply with the requirements of the study.

Exclusion Criteria to Enroll in the Initial Screening Phase:
1. Patients currently in the acute phase (<3 months) of any cancer treatment (surgery, chemotherapy, radiation therapy).
2. Patients with an identifiable diagnosis of substance abuse or dependence within 6 months prior to evaluation (except in full remission, and except for caffeine or nicotine dependence) as defined by DSM-IV criteria.
3. Patients with any significant unstable or inadequately treated co-morbid medical condition that would confound evaluation of CRF (e.g. diabetes, CHF, history of other cancers) as judged by the investigator.
4. Patients with any significant unstable or inadequately treated psychiatric disorder (except depressive and/or anxiety disorders) confounding appropriate CRF assessment as judged by the investigator.
5. Patients on multiple psychotropic medications.
6. Patients with a history of immunologically related diseases or diseases that could affect immune system function.
7. Patients regularly using immunosuppressive medications.
8. Patients with diseases that clearly affect the hypothalamic-pituitary-adrenocortical (HPA) axis function or patients on hormonal treatments affecting the HPA axis.
9. Any other condition, which, in the opinion of investigator, would make the patient, unsuited for enrollment or could interfere with the patient's participation in the study.

Additional Exclusion Criteria for Entering the Second, Comprehensive Assessment Phase:

Any of the following is regarded as a criterion for exclusion from the entering the second, comprehensive fatigue assessment phase of the study (based on the initial screening and laboratory assessment):

1. Patients with medically reversible causes of CRF such as anemia, hypothyroidism, and electrolyte abnormalities.
2. Patients with potentially treatable associated symptoms dominating the CRF scenario such as pain, which may have a causal relationship to CRF.

Criteria for Discontinuation:

Patients may be discontinued from the study treatment and assessments at any time. Specific reasons for discontinuing a patient from the study are as follows:

1. Voluntary discontinuation by the patient who is at any time free to discontinue participation in the study.
2. Severe non-compliance to the protocol as judged by the investigator.
3. Incorrect enrollment.
4. Patient is hospitalized due to any condition during the study period.
5. Greater than 20% improvement in fatigue scores on the MFI during the single-blind placebo run-in phase lasting one week.

Study Design:

The study is conducted in a standard randomized, double-blind, and placebo-controlled design format. It consists of four phases: an initial screening phase; a single-blind placebo run-in phase lasting one week; a 6-week double-blind, placebo-controlled treatment phase with taltirelin; and a one week taper and discontinuation phase.

Initial screening phase. Patients with a breast cancer or prostate cancer diagnosis meeting the initial inclusion and exclusion criteria undergo an initial screening with the brief fatigue inventory (BFI) in the oncology clinic setting. Patients experiencing severe level of fatigue (BFI≧7) are identified based on this screening. These patients undergo additional screening with a comprehensive interview and laboratory assessments (hemoglobin, hematocrit, thyroid stimulating hormone level and electrolytes) to identify and exclude patients with medically reversible or other treatable causes of fatigue (viz., anemia, hypothyroidism, electrolyte abnormalities, significant pain dominating the CRF scenario). A total of 40 patients with severe CRF and without any medically reversible causes of CRF are identified based on the initial screening process. Identified patients are randomized into two groups of 20 patients each, which are a study medication group and a placebo group.

Both groups undergo a comprehensive assessment to investigate different aspects of fatigue and quality of life. This assessment consists of multidimensional fatigue inventory (MFI) and the quality of life questionnaire, the 36-item short form survey (SF-36). Patients also are evaluated for depressive disorders and anxiety disorders using the hospital anxiety and depression scale (HADS). Patients are assessed for their overall status using the clinical global impressions severity of illness scale (CGI-S) and clinical global impressions improvement scale (CGI-I) at randomization and every 4 weeks during the intervention phase. Additionally, patients from both the groups undergo specific laboratory assessments related to immune and HPA axis. These laboratory assessments include selected serum markers for inflammatory activity and marker for HPA axis. The immune makers include interleukin-1 receptor antagonist (IL-1ra), soluble tumor necrosis factor receptor type II (sTNF-RII) and neopterin. Serum cortisol levels serve as a marker for the HPA axis. Heightened levels of one or more of these markers appear to be related to the pathophysiological mechanisms underlying CRF, and their reduction reflect the effect of treatment intervention.

Run-in phase. Following baseline assessment, all subjects are started on placebo tablets for a one-week single-blind placebo run-in phase. Subjects showing greater than a 20% improvement in fatigue scores on the MFI are disqualified from further study participation.

Treatment phase. The remaining subjects are entered in the 6-week double-blind treatment phase. During weeks one and two of this phase, subjects receive a 5 mg tablet of taltirelin or an identical-appearing placebo tablet at 0800 h. During weeks three though 6, all subjects receive taltirelin 5 mg or placebo at 0800 h and at 01300 h.

Taper phase. Finally, during the one week taper and discontinuation phase, subjects receive taltirelin 5 mg or placebo at 0800 h for 4 days and then all subjects receive placebo tablets for 3 days prior to final study evaluation. Patients undergo fatigue assessments with BFI and MFI every week during the study course. Patients also undergo assessments with SF-36, HADS and CGI-S at randomization, week 4 and at the end of intervention phase (week 8). CGI-I is performed at week 4 and at the end of intervention phase. At the end of the intervention phase, patients again undergo laboratory assessments for the same immune and HPA axis markers conducted at randomization.

Analysis:

TRH analog 10 mg is superior to placebo in improving cancer related fatigue as measured by change from baseline in mean fatigue scores assessed using BFI and MFI after 6 weeks of treatment.

TRH analog 10 mg is superior to placebo in improving quality of life as measured by change from baseline in mean quality of life scores assessed using SF-36 after 6 weeks of treatment Other variables are evaluated to assess efficacy including (1) the change from baseline in the mean of the CGI and CGI-S scores, and (2) markers of immune and HPA axis function as measured by assessment of IL-1ra, TNF-RII, neopterin and cortisol level to assess effect of TRH analog on the immune and HPA axis function.

While the 6-week (end of treatment) is primary, other time points are evaluated to assess the time course of treatment with taltirelin.

The analogs of thyrotropin-releasing hormone (TRH), herein referred to as "TRH analogs", comprise a group of metabolically stable peptidomimetic compounds disclosed in the prior art. In particular, the TRH analogs useful in the present invention include those analogs and prodrugs thereof disclosed in the following prior art references: U.S. Pat. Nos. 4,711,878; 4,563,306; 3,959,248: 5,151,497; 4,636,567; 4,610,821; 4,564,609; 4,719,207; 4,368,073; 4,299,821; 5,244,884; 4,877,784; 6,475,989; 5,686,420; 5,811,512; U.S. Patent Application Publ. Nos. 20030166944; 20030232966; U.S. Pat. Nos. 5,968,932; 4,956,364; 4,906,614; and 4,788,179, all of which disclosures of TRH analogs and prodrugs thereof are incorporated by reference.

The most preferred TRH analogs include the genera of compounds containing taltirelin, MK-771, JTP-2942, azetirelin (M-14637), positirelin (RGH-2022), and montirelin (CG-3703), all of which are described in one or more of the US Patents referenced hereinabove. The most preferred TRH analogs useful in the present invention are taltirelin and montirelin, having the following formulae respectively.

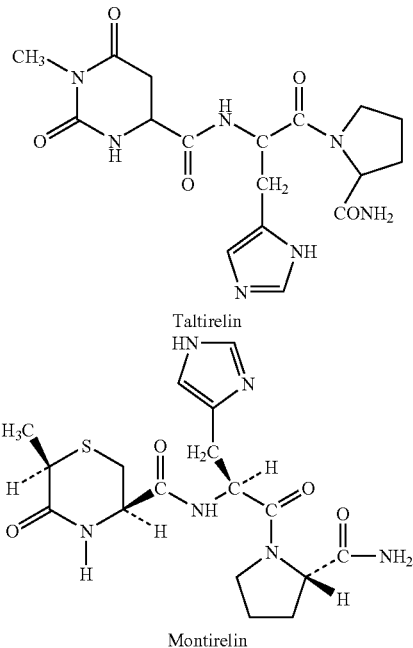

Taltirelin

Montirelin

TRH or prodrug or the TRH analog or prodrug may be administered as such as a free base, hydrate, or in the form of a salt with a pharmaceutically acceptable salt. The TRH and prodrugs of TRH and TRH analogs and prodrugs of TRH analogs can be used alone or in combination with pharmacologically acceptable carriers, additives, or excipients, the proportions of which are determined by solubility and chemical nature of the compound, chosen route of administration, and standard medical practice.

In one embodiment of the present invention, pharmaceutical compositions include a therapeutically effective amount of any one or more of the TRH and prodrugs of TRH or TRH analogs or prodrugs of TRH analogs of the invention in pharmaceutical dosage form to treat and prevent a cancer-related fatigue. The therapeutically effective amount will vary with the specific TRH analog or prodrug utilized, if TRH itself or a prodrug of TRH is used, the pharmacokinetics of the agent used, the severity of the fatigue, as well as the patient treated.

TRH or prodrugs of TRH or the TRH analogs or prodrugs of TRH analogs used according to the present invention, whether administered separately or as a pharmaceutical composition of the present invention, can be formulated according to known methods for preparing pharmaceutically useful compositions.

Pharmaceutical compositions based upon TRH or these TRH analogs may be formulated for a variety of routes of administration, including, for example, orally-administrable forms such as tablets, capsules or the like, or via parenteral, intravenous, intramuscular, transdermal, buccal, subcutaneous, suppository, or other route. In certain pharmaceutical dosage forms, certain of the present TRH analogs may be more appropriate than other compounds, depending upon the route of administration and the targeted site within the patient. The compositions of the invention can be formulated so as to provide quick, sustained or delayed release of the active ingredient after administration to the patient by employing procedures known in the art. Formulations are described in a number of sources that are well known and readily available to those skilled in the art. For example, Remington's Pharmaceutical Science (Martin E W [1995] Easton Pa., Mack Publishing Company, 19.sup.th ed.) describes formulations, which can be used in connection with the present invention.

TRH or the TRH analogs may be administered in a pharmaceutical composition comprising TRH or the TRH analog or prodrug of TRH or the TRH analog in combination with a pharmaceutically acceptable carrier.

The term "pharmaceutically acceptable carrier" includes, for example, pharmaceutically acceptable carriers such as the following: solid carriers such as lactose, magnesium stearate, terra alba, sucrose, talc, stearic acid, gelatin, agar, pectin, acacia or the like; and liquids such as vegetable oils, arachis oil and sterile water, or the like. However, this listing of pharmaceutically acceptable carriers is not to be construed as limiting.

In preparing pharmaceutical compositions in oral dosage form according to the present invention, any one or more of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, tablets or capsules may be enteric-coated or sustained release by standard techniques.

Where appropriate, dosage unit formulations for oral administration can be microencapsulated. The formulation can also be prepared to prolong or sustain the release as for example by coating or embedding particulate material in polymers, wax, or the like.

Formulations suitable for parenteral administration include, for example, aqueous sterile injection solutions, which may contain antioxidants, buffers, bacteriostats, and solutes that render the formulation isotonic with the blood of the intended recipient; and aqueous and nonaqueous sterile suspensions, which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the present invention could include other agents conventional in the art having regard to the type of formulation in question.

Topical pharmaceutical compositions may be in the form of a solution, cream, ointment, mousse, gel, lotion, powder or aerosol formulation adapted for application to the skin. Topical preparation containing TRH or prodrug of TRH or the TRH analogs or prodrugs of TRH analogs of the subject invention can be admixed with a variety of carrier materials or pharmaceutically acceptable excipients well known in the art. When the excipient serves as a diluent, it can be a solid, semi-solid, or liquid, which acts as a vehicle, carrier, or medium for the active ingredient. Thus, the compositions can be in the form of powders, suspensions, emulsions, solutions, syrups, alcoholic solutions, ointments, topical cleansers, cleansing creams, skin gels, skin lotions, mousses, roll-ons, aerosol or non-aerosol sprays in cream or gel formulations and soft gelatin capsules For parenteral formulations, the carrier may comprise sterile water or aqueous sodium chloride solution in combination with other ingredients that aid dispersion, such as ethanol and other pharmaceutically acceptable solvents. Of course, where solutions are to be used and maintained as sterile, the compositions and carrier must also be sterilized. Injectable suspensions may also be prepared, in which case appropriate liquid carriers, suspending agents and the like may be employed.

Example 1

Oral Tablet Formulation

Tablets are prepared comprising the following ingredients in parts by weight:

| | |
|---|---|
| taltirelin hydrate | 10 parts |
| lactose monohydrate | 64 parts |
| corn starch | 20 parts |
| polyvinylpyrrolidone (Polyvidone K 30) | 5 parts |
| magnesium stearate | 1 part |

The active compound, lactose monohydrate and corn starch are sieved through a 0.63 mm sieve, mixed in a cube blender for 10 minutes, granulated with an aqueous solution of polyvinylpyrrolidone in water (50 g in 200 ml of water), dried, sized through an 0.8 mm sieve together with the magnesium stearate, mixed and pressed into tablets having a diameter of 6 mm and an average weight of 100 mg using a conventional tablet press such as a Korsch EK 0 eccentric press.

Example 2

Oral Liquid Formulation

An orally administrable liquid formulation is prepared comprising the following ingredients in parts by weight:

| | |
|---|---|
| taltirelin hydrate | 10 parts |
| potassium sorbate | 10 parts |
| sodium citrate | 6 parts |
| citric acid | 2 parts |
| sodium chloride | 2 parts |
| sucrose | 200 parts | sufficient water to solution volume containing 10 g taltirelin hydrate per liter of solution. The solid ingredients were all dissolved in water, filtered through a 0.23 micron membrane and filled into bottles. 1 ml of the resulting solution contained 10 mg of taltirelin. Individual dosing can be achieved by administering individual volumes of the solution to the patient.

Example 3

Nasal Spray Formulation

A nasal spray formulation is prepared comprising the following ingredients in parts by weight:

| | |
|---|---|
| TRH or taltirelin hydrate | 80 parts |
| benzalkonium chloride | 1 part |
| polyoxyethylene (20) sorbitan monooleate (Polysorbate 80) | 80 parts |
| sodium carboxymethylcellulose (Tylose.TM. C 30) | 80 parts |
| disodium hydrogen phosphate | 72 parts |
| sodium dihydrogen phosphate | 32 parts |
| dextrose | 240 parts | purified water to volume containing 10 g taltirelin hydrate per liter of solution. The solid ingredients were all dissolved in the water, filtered through a 0.5.micron membrane and, filled into bottles topped by a spray pump with a volumetric dispensing chamber of 100 microliter for nasal administration.

Suppositories containing TRH or prodrug of TRH or a TRH analog or prodrug of TRH analog ingredient may be prepared by melting 95 g of a commercially available suppository base at about 40 to 45 degree C., adding 3 g of salicylic or mandelic acid, followed by adding, while stirring, 2 g of the API ingredient and pouring the mixture into molds.

REFERENCES

1. Atkinson A, Barsevick A, Celia D, et al. NCCN practice guidelines for cancer-related fatigue. *Oncol New York.* 2000; 14(11A suppl 10): 151-61
2. Bower J E, Ganz P A, Desmond K A, Rowland J H, Meyerowitz B E, Belin T R. Fatigue in breast cancer survivors: occurrence, correlates, and impact on quality of life. *J Clin Oncol.* 2000; 18(4): 743-53
3. Bower J E, Ganz P A, Aziz N, Fahey J L. Fatigue and proinflammatory cytokine activity in breast cancer survivors. *Psychosom Med.* 2002; 64(4): 604-11
4. Curt G A, Breitbart W, Celia D, Groopman J E, Horning S J, Itri L M, Johnson D H, Miaskowski C, Scherr S L, Portenoy R K, Vogelzang N J. Impact of cancer-related fatigue on the lives of patients: New findings from the fatigue coalition. *Oncologist* 2000; 5: 353-60
5. De Jong N, Candal M J, Schouten H C, Huijer Abu-Saad H, Courtens A M. Fatigue in patients with breast cancer receiving adjuvant chemotherapy: a review of literature. *Cancer Nurs.* 2002; 25 (4): 283-297.
6. Demetri G D, Kris M, Wade J, Degos L, Cella D. Quality-of-life benefit in chemotherapy patients treated with epoetin alfa is independent odf disease response or tumor type: results from a prospective community oncology study. Procrit study group. *J Clin. Oncol.* 1998; 16(10):3412-25
7. Dow K H, Ferrell B T, Leigh S. An evaluation of the quality of life among long-term survivors of breast cancer. *Breast Cancer Res Treat* 1996; 39:261-273
8. Gary K A, Sevarino K A, Yarbrough G G, Prange A J Jr, Winokur A. The thyrotropin-releasing hormone (TRH) hypothesis of homeostatic regulation: implications for TRH-based therapeutics. *J Pharmacol Exp Ther.* 2003; 305(2):410-6.
9. Glaus A, Crow R, Hammond S. A qualitative study to explore the concept of fatigue/tiredness in cancer patients and healthy individuals. *Eur J Cancer Care* (English language ed.) 1996; 5 (suppl 2): 8-23
10. Greenberg D G, Gray J L, Mannix C M, Eisenthal S, Carey M. Treatment related fatigue and serum interleukin-1 levels in patients during external beam irradiation for prostate cancer. *J Pain Symptom Manage* 1993; 8: 196-200

11. Gutstein H B. The biologic basis of fatigue. *Cancer* 2001; 92(6 Suppl): 1678-83
12. Holly S. Cancer-related fatigue-suffering a different fatigue. *Cancer Pract.* 2000; 8(2): 87-95
13. Irvine D M, Vincent L, Bubela N, Thompson L, Graydon J E. The prevalence and correlates of fatigue in patients receiving treatment with chemotherapy and radiotherapy: a comparison with the fatigue experienced by healthy individuals. *Cancer Nurs.* 1994; 17:367-78
14. Kunkel E J S, Bakker J R, Myers R E, Oyesanmi O, Gomella L G. Biopsychosocial aspects of prostate cancer. *Psychosomatics* 2000; 41: 85-94
15. Kurzock R. The role of cytokines in cancer-related fatigue. *Cancer* 2001; 92(6 Suppl): 1684-8
16. Mendoza T R, Wang X S, Cleeland C S, Morissey M, Johnson B A, Wendt J K, Huber S L. The rapid assessment of fatigue severity in cancer patients: use of the Brief Fatigue Inventory. *Cancer* 1999; 1186-96
17. Mock V. Fatigue management: Evidence and guidelines for practice. *Cancer* 2001; 92(6 Suppl): 1699-1707
18. Portenoy R K, Itri L M. Cancer-related fatigue: Guidelines for evaluation and management. *Oncologist* 1999; 4:1-10
19. Richardson A. Fatigue in cancer patients: a review of the literature. *Eur J Cancer Care* (English language ed.) 1995; 4:20-32
20. Smets E M, Garssen B, Cull A, de Haes J C. The multidimensional Fatigue Inventory (MFI): psychometric qualities of an instrument to assess fatigue. *J of Psychosomat Res;* 39(3):315-25
21. Smets E M, Garssen B, Cull A, de Haes J C. Application of the multidimensional fatigue inventory (MFI-20) in cancer patients receiving radiotherapy. *Br J Cancer* 1996; 73(2): 241-5
22. Stone P, Richards M, A'Hern R, Hardy J. A study to investigate the prevalence, severity and correlates of fatigue among patients with cancer in comparison with a control group of healthy volunteers without cancer. *Ann Oncol* 2000; 11:561-7
23. Stone P, Richards M, Hardy J. Fatigue in patients with cancer. *Eur J Cancer* 1998; 34(11): 1670-76
24. Valentine A D and Meyers C A. Cognitive and mood disturbances as causes and symptoms of fatigue in cancer patients. *Cancer* 2001; 92(6 Suppl): 1684-8
25. Visser M R M, Smets E M A. Fatigue, depression and quality of life in cancer patients: how are they related? *Support Care Cancer* 1998; 6: 101-8
26. Ware J E Jr and Sherbourne C D. A 36-item Short Form Health Survey (SF-36): Conceptual framework and item selection. *Med Care* 1992; 30: 473-83
27. Yamamura M, Suzuki M., Matsumoto K. Synthesis and pharmacological action of TRH analog peptide (Taltirelin). *Nippon Yakurigaku Zasshi.* 1997; 110 Suppl 1:33P-38P.
28. Zigmond A S, Snaith R P. The hospital anxiety and depression scale. *Acta Psychiatr Scand* 1983; 67:361-70

We claim:

1. A method for the treatment of idiopathic cancer-related fatigue in human patients suffering from a neoplastic disorder, comprising administering to said patient a cancer-related fatigue relieving amount of thyrotropin-releasing hormone or a thyrotropin-releasing hormone analog or a pharmaceutically acceptable salt thereof or a hydrate thereof or a prodrug thereof.

2. A method according to claim 1, wherein said patients are suffering from a severe and persistent fatigue that is not alleviated by rest.

3. A method for the alleviation of idiopathic cancer-related fatigue in subjects afflicted with a neoplastic disorder and who have received treatment therefor, comprising the administration of a therapeutically effective cancer-related fatigue-relieving amount of thyrotropin-releasing hormone or a peptidomimetic analog of thyrotropin-releasing hormone.

4. A method according to claim 1, wherein said patients have undergone surgery, radiation treatment, and/or have been treated with chemotherapeutics and/or immunotherapeutic agents.

5. A method according to claim 3 wherein said subjects exhibit HPA axis dysfunction and pro-inflammatory activity.

6. A method according to claim 3 wherein said peptidomimetic is a compound according to the formula

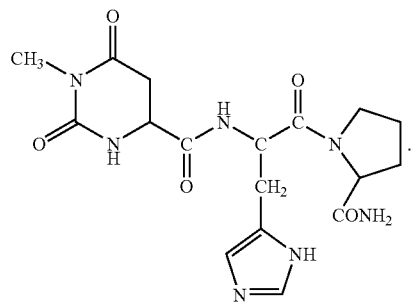

7. A method according to claim 3 wherein about 0.01 mg/kg to about 2 mg/kg of said peptidomimetic is administered from once to three times a day.

8. A method according to claim 3 wherein about 5 mg to about 30 mg of said peptidomimetic is administered from once to three times a day.

9. A method according to claim 3 wherein thyrotropin-releasing hormone or said peptidomimetic is administered orally, transdermally, via inhalation, injection, nasally, rectally or via a sustained release formulation.

10. A method according to claim 3 wherein thyrotropin-releasing hormone or said thyrotropin-releasing hormone analog is administered to said patient for a period of time that relieves said cancer-related fatigue, and for a period of time thereafter is treated with decreasing dosages to attain drug free homeostasis.

* * * * *